(12) United States Patent
Wei (10) Patent No.: US 8,853,267 B2
(45) Date of Patent: Oct. 7, 2014

(54) N-ALKYLCARBONYL-AMINO ACID ESTER COMPOUNDS AND THEIR USE FOR SKIN IRRITATION, ITCH, AND PAIN

(76) Inventor: Edward Tak Wei, Berkeley, CA (US)

(\*) Notice: Subject to any disclaimer, the term of this patent is extended or adjusted under 35 U.S.C. 154(b) by 523 days.

(21) Appl. No.: 12/930,794

(22) Filed: Jan. 18, 2011

(65) Prior Publication Data

US 2011/0152366 A1 Jun. 23, 2011

Related U.S. Application Data

(63) Continuation-in-part of application No. 11/910,185, filed on Sep. 28, 2007, now abandoned.

(51) Int. Cl.
*A61K 31/215* (2006.01)
*A61P 17/00* (2006.01)

(52) U.S. Cl.
USPC ........................................ 514/529; 424/78.05

(58) Field of Classification Search
None
See application file for complete search history.

(56) References Cited

U.S. PATENT DOCUMENTS 4,136,163 A * 1/1979 Watson et al. .................. 424/54
2008/0227857 A1 * 9/2008 Wei ............................... 514/473

\* cited by examiner

*Primary Examiner* — Frederick Krass
*Assistant Examiner* — Michael P Cohen (57) ABSTRACT

The present invention generally relates to refreshing, soothing, and cooling compounds that affect sensory processes. More particularly, the present invention pertains to certain N-alkylcarbonyl-D-Ala-esters compounds as described herein; compositions and articles comprising such compounds; and methods of treatment, for example, methods of reducing skin irritation, itch, and/or pain.

2 Claims, 2 Drawing Sheets

N-ALKYLCARBONYL-AMINO ACID ESTER COMPOUNDS AND THEIR USE FOR SKIN IRRITATION, ITCH, AND PAIN

RELATED APPLICATIONS

This application is a continuation-in-part of U.S. patent application Ser. No. 11/910,185, published as 20080227857, filed Mar. 23, 2006, inventor Wei, entitled "N-Alkylcarbonyl-Amino Acid Ester and N-Alkylcarbonyl-Amino Lactone Compounds and Their Use', incorporated by reference.

RELATED APPLICATIONS

This application is related to:
U.S. Provisional Application No. 60/667,166 filed 29 Mar. 2005;
U.S. Provisional Application No. 60/683,384 filed 20 May 2005;
U.S. Provisional Application No. 60/702,505 filed 26 Jul. 2005;
U.S. Provisional Application No. 60/772,374 filed 9 Feb. 2006;
the contents of each of which are incorporated herein by reference in their entirety.

TECHNICAL FIELD

The present invention generally relates to refreshing, soothing, and cooling compounds that affect sensory processes. More particularly, the present invention pertains to certain N-alkylcarbonyl-amino acid ester compounds; compositions and articles comprising such compounds; and methods of treatment, for example, methods of alleviating the discomforts of irritation, itch, and pain on the skin.

BACKGROUND

Menthol and menthol-like compounds are used in toiletries, confectionery, comestibles, and over-the-counter medications as ingredients to refresh, cool, flavor, and counter-irritate the skin and the mucous membranes of the mouth and upper airways. Menthol's utility in relief of sensory discomfort is, however, limited by its short duration of action and by its multimodal actions on sensory processes—including odor, harshness of taste, and irritation. Some commercial over-the-counter anti-itch and analgesic preparations contain menthol as an active ingredient. For example, "Anti-Itch Medicated Cream" from Walgreens contains 1% menthol and 1% pramoxine hydrochloride and extra strength Icy Hot® Patch for muscular pain contains 5% menthol in an occlusive bandage.

About three decades ago, a group of scientists synthesized over 1200 compounds in an attempt to find cooling agents that had properties better than menthol. Their results were summarized in a paper (Watson et al., "New compounds with the menthol cooling effect," J. Soc. Cosmet. Chem., 29: 185-200, 1978). From this research, an N-alkyl-cycloalkyl- and an N-alkyl-alkyl carboxamide, WS-3, WS-5, and WS-23, were brought to the market and are used as additives for confectionery, comestibles, (e.g., candy, chewing gum), and toiletries. An active ingredient for skin itch/irritation and pain was not identified or developed.

In U.S. Pat. No. 4,178,459 (11 Dec. 1979), Watson et al. described cooling properties of some N-alkoxycarbonylalkyl-substituted p-menthane-carboxamides. The designation in '459 is silent with respect to stereoisomerism on the alanine moiety of alanyl O-esters. The recent information on cooling agents used for topical applications was reviewed by M. B. Erman ("Cooling agents and skin care applications," Cosmetics & Toiletries, 120: 105-118, May 2005; "Progress in physiological cooling agents," Perfumer & Flavorist, 29: 34-50, 2004) and by P. Jacobs and W. Johncock ("Some like it cool," Parfumerie and Kosmetik, 80: 26-31, 1999).

None of the menthol-like compounds currently known to the art have the potency or duration of action to qualify them as possible medications for use in pathological skin itch and pain.

SUMMARY OF THE INVENTION

One aspect of the present invention pertains to certain N-alkylcarbonyl-amino acid ester compounds, as described herein.

Another aspect of the invention pertains to a composition comprising such a compound and a delivery vehicle (e.g., for delivering the compound to a human).

In one embodiment, the delivery vehicle is a pharmaceutically acceptable carrier or diluent. for dermatological applications.

One aspect of the present invention pertains to use of such a compound in the manufacture of a medicament for use in a method of treatment.

In one embodiment, the treatment is alleviation of skin itch and/or pain (e.g., wherein the contacting delivers an amount of the compound that is therapeutically effective for alleviation of skin itch and/or pain).

As will be appreciated by one of skilled in the art, features and preferred embodiments of one aspect of the invention will also pertain to other aspect of the invention. Other advantages and aspects of the invention will be understood by reading the following detailed description and the accompanying claims.

DETAILED DESCRIPTION

A class of compounds that is suitable to be used as an active ingredient in preparations for use on the skin to treat itch/pain has been found.

These compounds are suitable, for example, for use as therapeutic agents, to reduce discomfort such as irritation, itch and pain.

These compounds have one or more of the following properties:
- a refreshing, soothing, and cooling action on the skin, and, in pathological states, exert an anti-irritant, anti-pruritic, and/or anti-nociceptive effect;
- a rapid onset of action of less than about 5 minutes (e.g., from 0.5 to 5 minutes), when applied onto the skin at a concentration of 2 to 20 mg/ml;
- a duration of action that exceeds 1 hour (see FIG. 2).
- a potent cool, soothing, and refreshing sensation when applied onto the skin that counteracts irritative stimuli that causes scratching and/or pain.

These compounds have clinical applications for:
- itch of allergic origin, e.g. atopic eczema or contact dermatitis, for atopic eczema the itch site is frequently localized to the skin of the flexures of the elbow and knees (because of sweating), and on facial skin, especially around the neck and ears.
- dry skin itch (xerosis of the elderly), e.g. associated with age, predominantly on the legs (18% of body surface), but also on the torso, and covering a larger surface area
- itch from psoriasis, e.g. scalp, and the elbow and knee joints, and other forms of dermatoses.
- orbital and ocular itch, e.g. conjunctivitis The structure of the compounds of this discovery are shown in Formula 1.

Formula (1)

wherein:
R is methyl, ethyl, n-propyl, or n-butyl

The D-configuration of the α-carbon has the effect of increasing potency and duration of action, and of producing a selective refreshing coolness with the absence of tissue irritation.

These preferred compounds are shown as No. 1, No. 2, No. 3 and No. 5 in Table 1. In the text of this application, compounds will be identified by the No. or by an abbreviation derived from the nature of ester, e.g. D-Ala-OEt as being equal to No. 2, without specifying that it attached to the p-menthoyl moiety [(R)-2-[((1R,2S,5R)-2-isopropyl-5-methyl-cyclohexanecarbonyl)-].

TABLE 1

Compounds studied for the topical treatment of skin itch/pain.

| | | | |
|---|---|---|---|
| 1 D-Ala-OMe | (R)-2-[((1R,2S,5R)-2-isopropyl-5-methyl-cyclohexanecarbonyl)-amino]-propionic acid methyl ester | |  |
| 2 D-Ala-OEt | (R)-2-[((1R,2S,5R)-2-isopropyl-5-methyl-cyclohexanecarbonyl)-amino]-propionic acid ethyl ester | |  |
| 3 D-Ala-OnPr | (R)-2-[((1R,2S,5R)-2-isopropyl-5-methyl-cyclohexanecarbonyl)-amino]-propionic acid n-propyl ester | |  |
| 4 D-Ala-OiPr | (R)-2-[((1R,2S,5R)-2-isopropyl-5-methyl-cyclohexanecarbonyl)-amino]-propionic acid i-propyl ester | |  |

TABLE 1-continued

Compounds studied for the topical treatment of skin itch/pain.

| | | |
|---|---|---|
| 5 D-Ala-OnBu | (R)-2-[((1R,2S,5R)-2-isopropyl-5-methyl-cyclohexanecarbonyl)-amino]-propionic acid n-butyl ester |  |

The compounds of Formula 1, designated long-acting N-alkylcarbonyl D-Alanyl acid esters (NADE) are distinguished from other N-alkylcarbonyl-amino acid esters (e.g., WS-5 and WS-31) and N-alkyl substituted carboxamides (e.g., WS-3, WS-12, WS-23) which are known to have cooling properties, and the two (WS-3 and WS-23) that are commercially used in comestibles, confectionery, and toiletries.

Figure 1:
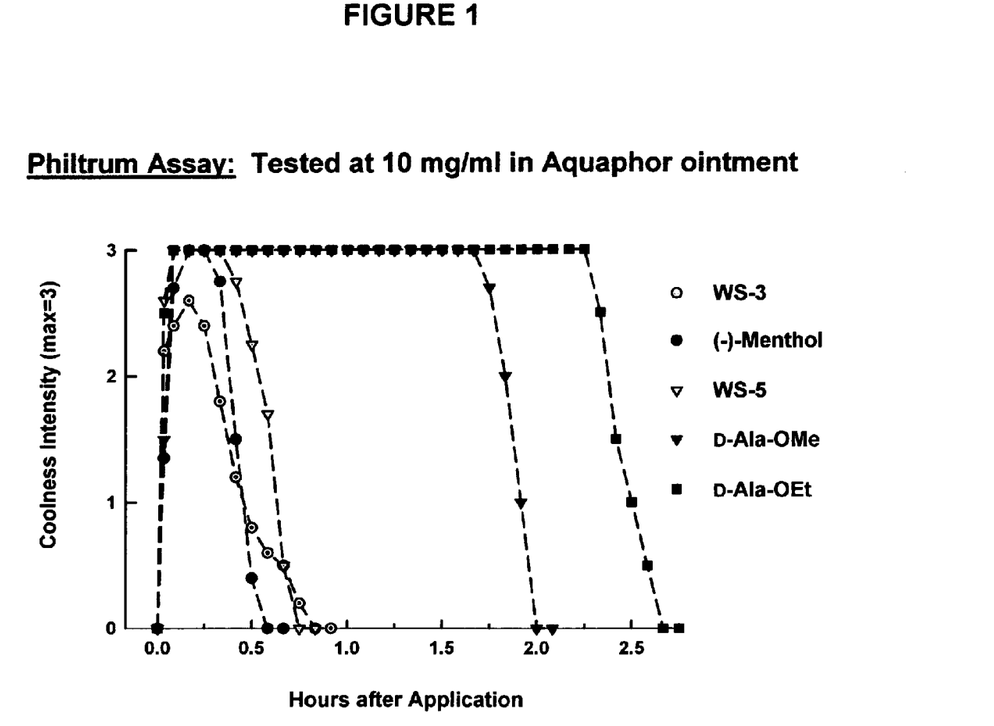
FIG. 1 is a graph showing duration of cooling (hours) for five compounds (in order, left to right): WS-3, (−)-menthol, WS-5, D-Ala-OMe, and D-Ala-OEt. The durations of cooling effects of known agents, e.g., (−)-menthol, WS-3, and WS-5 are ≤0.5 hr, and relatively short compared to the D-Ala-OMe and D-Ala-OEt of >1.5 hr. Test substances were dissolved 10 mg/ml in Aquaphor® ointment and applied to the philtrum skin. The presence the D-Ala configuration increases duration of action and these two compounds are examples of the preferred embodiments of this invention.
Figure 2:
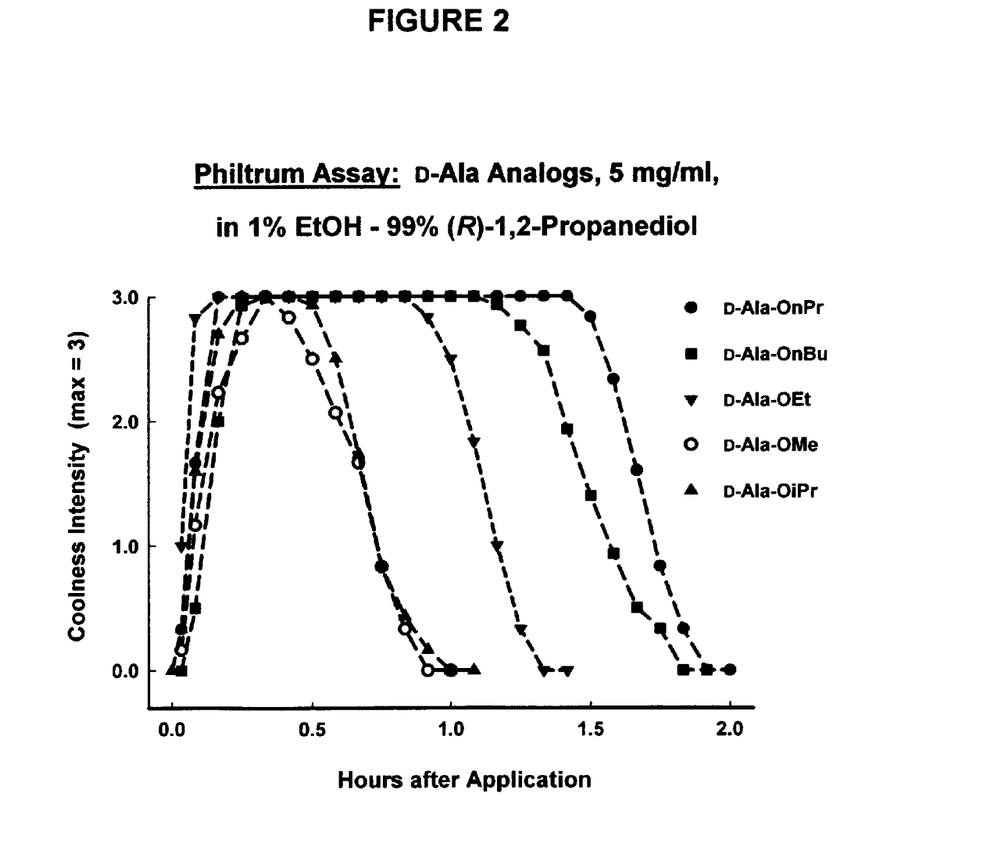
FIG. 2 is a graph showing duration of cooling (hours) for five compounds (in order, left to right): D-Ala-OMe, D-Ala-OiPr, D-Ala-OEt, D-Ala-OnBu, and D-Ala-OnPr. The test substance is dissolved in 1% EtOH-99% (R)-1,2-propanediol and ~0.03 ml is applied on the philtrum skin, a surface area of ~11 $cm^2$. For a 5 mg/ml solution, the applied dose is ~0.15 mg/11 $cm^2$=0.014 mg/$cm^2$. The (R)-1,2-propanediol delivery vehicle is an alternative to the Aquaphor® ointment. The surprising long durations of action of the D-Ala-OEt, D-Ala-OnPr, and D-Ala-OnBu analogs are noted and are examples of the preferred embodiments of this invention.

As shown in U.S. 20080227857 of which this application is a continuation-in-part, WS-3, WS-5, WS-12, WS-23 and WS-31, have a short duration of action (less than 1 hour) at ~10 mg/ml on the skin or slow onset (more than 5 minutes). By contrast, the preferred long-acting NADE compounds applied to the skin deliver a robust cooling sensation, with rapid onset, and a duration of action lasting more than 1 hr, actions that have not been previously recognized (FIG. 1 and FIG. 2).

The potency, duration, and selectivity (absence of irritation) of action are increased for the alanine derivative with the α-carbon in the D-configuration. The alanine enantiomers with the α-carbon in the L-configuration are virtually inactive. Thus, based on the results in FIG. 2 and Table 4, I estimate, in an equal mixture (racemic) of D-Ala and L-Ala enantiomers, it is likely that ~90% of the skin bioactivity is contributed by the D-enantiomer.

Due to their prolonged activity, the compounds, compositions, and articles may be used therapeutically, for example, to reduce discomforts associated with pathophysiological manifestations of skin itch and pain.

These compounds may be delivered to the skin to counter-act irritation, itch and pain in therapeutic situations where prolonged relief of sensory discomfort is desired such as in atopic eczema, psoriasis, and xerosis.

Currently, there are no topical medications approved in this category for therapeutic relief of skin disorders, although the demand exists for such substances. The potent D-Ala compounds of Formula 1, with selective cooling and refreshing actions increase the scope of agents that may be used for therapy of the skin.

The specific D-configuration of the α-carbon in Ala that confers the desired properties of increased potency and the presence of refreshing cooling without irritation were unexpected and surprising and not known in the prior art.

Non-Technical Description of Inventive Concept

Molecules have been identified with potent and prolonged activation of cooling sensations on the keratinized skin. These molecules are qualitatively and quantitatively unlike (−)-menthol and menthol-like congeners which act for less than 20 minutes. In skin itch and pain, it was observed that these NADE compounds exert prolonged anti-nociceptive activity when the sensations of coolness no longer reach conscious perception, and that repeated applications of the NADE compounds can silence and extinguish nociception. The long-acting NADE compounds are active at concentrations of 5 to 10 mg/mL when delivered topically in a vehicle at single doses of less than 0.5 mg per dose. The NADE compounds have a rapid onset of action (from about 0.5 to about 5 minutes), and their actions were revealed by testing on the facial skin of subjects in various vehicles (ointments and (R)-1,2-propanediol).

Pharmacology and Mechanisms of Action of N-Alkylcarbonyl-D-Ala Esters (NADE) in Counter-Acting Skin Discomfort Itch, also called pruritus, is defined as the sensation associated with the urge to scratch. Itch is a familiar sensation and scratching is common to humans and (especially) to fur-coated animals. Scratching is an episodic bout of vigorous motor activity. Scratching is designed to remove irritants from the skin and, in a natural milieu, has survival value. Mechanoreceptors are activated by scratching, but it is not necessary to precisely scratch the point source of the itch to obtain relief. Adjacent sites will suffice. This happens because, in the skin, sensory inputs converge, so the area innervated by a single spinal nerve (called a dermatome) receives inputs from adjacent dermatomes. The sensations from one locale can thus influence the adjacent site because there is somatotopic overlap in the sensory projections.

Itch may be intense and scratching sufficiently frequent to adversely affect the quality of life. Pain, unlike itch, is not relieved by the mechanosensations caused by scratching. Both pain and itch reflect some aspect of cellular irritation or injury.

The skin is composed of three layers: the epidermis, the dermis and the subcutaneous fatty tissue. The epidermis varies in thickness from 0.15 to 0.80 mm and its outermost part, called the stratum corneum (horny layer) is built of several layers of flattened, dehydrated, keratinised cells. The dermis is 3 to 5 mm thick and it contains collagen fibres, blood and lymphatic vessels, hair follicles, and sebaceous and sweat glands. The epidermis and the dermis contain the sensory nerve endings (most likely unmyelinated C-fibers) that detect and transmit the signals for irritation, itch and pain. The peripheral receptors for nociceptive stimuli—irritation, itch, and pain—are varied. For example, irritation is linked to TRP-A1 channels, and heat/pain is linked to TRP-V1. Voltage-gated sodium channels, e.g. Nav-1.7, 1.8, 1.9, in peripheral sensory neurons are linked to pain transmission. Histamine and proteases in skin are important mediators for triggering itch.

Cooling is able to attenuate itch/pain because it indirectly "gates" the processing/perception of noxious stimuli converging in the central nervous system. This attenuation mechanism of action has been described in U.S. 20080227857 and is not modality specific for itch or pain, but works on both. One unusual feature noted in the studies here is that the cooling sensation can be of short duration, e.g. about 10 min, (as shown in the Studies on the scalp or on the skin covering the elbow process), yet the antipruritic and antinociceptive effects can last for 8 or more hours. This "memory trace" action is most unusual and surprising, but may be explained if it is clearly recognized that the antipruritic and antinociceptive actions are indirect, acting via a gating mechanism. There is no direct drug action of the cooling agent on itch or pain receptors in the skin. It is the cooling Aδ/C-fiber transmitted sensory signals that are triggering release an inhibitory process (perhaps via metabotropic glutamic acid receptors) that is gating the itch/pain signals. The gating mechanism in the central nervous system may desensitize, hyper-polarize, or otherwise modulate the sensitivity of central neurons for an extended period of time. That is, there is a lingering memory trace in the brain that attenuates the nociceptive sensations and the urge to scratch.

Current drug therapies for the treatment of itch include the anti-inflammatory steroids, sedative antihistamines, κ-opioid agonists, and some tricyclic compounds, such as doxepin hydrochloride. Other drugs such as camphor, menthol, phenol, salicylic acid, tar, capsaicin, and petrolatum are part of dermatological preparations but have uncertain anti-pruritic effect. Topical steroids are most widely used for dermatoses and have short-term effectiveness for reducing inflammation. Prolonged use, however, results in thinning of the skin and the possibility of super-infection. Antinociceptive drugs applied to the skin include the cyclooxygenase inhibitors such as ibuprofen, local anesthetics, and menthol. There is need for new medications, simply applied, that is not invasive on brain chemistry, have fewer side effects, and which will control skin itch/pain for at least four hours to allow the individual to stop scratching or complain of pain.

The significance of itching and skin discomfort (irritation, burning sensations, and pain) in clinical conditions is illustrated by conditions such as atopic dermatitis, psoriasis, and dry skin itch of the elderly.

Atopic dermatitis is a chronic inflammatory skin disorder exhibited by individuals with a hereditary predisposition to a lowered cutaneous threshold to pruritis, often accompanied by allergic rhinitis, hay fever, and asthma. The condition is characterized by extreme itching, leading to continual scratching and rubbing of the skin that in turn results in skin injury. In infants (infantile eczema), there is a predilection for occurrence of itch on the cheeks, which may extend to other areas of the body. In older children, adolescents and adults, it is found chiefly on the flexural surfaces, especially on the antecubital (elbow) and popliteal (knee) areas, and on the neck, eyelids, and wrists and behind the ears. Affected children will scratch even when asleep for up to 2 out of 8 hours of sleep (versus a few minutes for normal children) and the excoriations can lead to bleeding and infection. Atopic dermatitis and eczema, if sufficiently severe, can lead to death. Less serious, but uncomfortable and often painful symptoms associated with atopic dermatitis include swelling, redness, blisters, crusting, ulceration, pain, scaling, skin cracking, hair loss, scarring, or oozing of fluid involving the skin, eye, or mucous membranes. Under current therapy, various ointments, topical anti-inflammatory glucocorticosteroids, and immunosuppressants are partially effective in treating this condition.

Dry skin itch (or xerotic eczema) occurs frequently in the elderly affecting ~30% of people aged ~78+years residing in nursing homes. With age sweat glands and sebaceous glands decline in function, with less sebum secretion and loss of protective barrier functions on the skin. The skin dysfunction type of lesion occurs more frequently on the legs and torso and frequent scratching (itch-scratch cycle) can lead to further skin pathology and inflammation. Longterm management is difficult and is focused initially on removal of the pruritic stimuli followed by better skin care.

Psoriasis affects ~2% of the US population. Plaque-type psoriasis, or psoriasis vulgaris, is the most common form affecting 75 to 80% of the psoriasis patients. About 70% of plaque-type patients complain of itch, skin pain, or burning sensations, especially when the scalp is involved.

Bioassays of N-Alkylcarbonyl-Alanyl Esters(NADE)

Psychic events such as refreshment, soothing, cooling, irritation, itch, and pain cannot be verbalized by animals (animals cannot say "it feels cold", "ouch", or that "it itches"). Hence, the sensory effects of chemicals in animals must be indirectly inferred. Receptor assays, based on cells transfected with the genes for proteins associated with thermosensation (e.g., TRP-M8, TRP-A1, TRP-V1) may be used as a model of sensory processes. The receptor assays yield quantitative data. Here we compared D-Ala-OEt (No. 2 in Table 1) to L-Ala-OEt in a TRP-M8 assay (data from Prof. D. Bautista's laboratory at the University of California at Berkeley) and found $EC_{50}$ of 0.5 μM and 18.0 μM, respectively. Thus, the D-Ala-OEt is 36-fold more potent than L-Ala-OEt, and in a racemate would account for 97% (18/18.5×100) of the bioactivity. The in vitro assay gives no information on onset and offset of action, but yields information on comparative potency of the two enantiomers. Further evaluation of the pharmacological properties of the test substances were based on direct tests in human subjects.

Philtrum Assay. To find a topical antipruritic or antinociceptive agent, one method is to dissolve a test substance in an ointment (e.g. Aquaphor®, which is 41% petrolatum, and the rest mineral oil, ceresin and lanolin alcohol) and singly applying the ointment (40 to 70 mg) onto the skin surface using a plastic stick. A reliable place for topical application is the skin above the upper lip (above the vermilion border of the lips), on the philtrum, lateral to the philtrum until the nasolabial folds, and on the lower nostrils (subnasale). This part of the face is known to be densely innervated with cold receptors, second only to the surfaces of the eyeball and anogenitalia. At this locus, cool and cold sensations in the skin may be experienced and rated for time of onset and intensity. An alternative delivery vehicle is (R)-1,2-propanediol (see below).

The intensity of the subjective skin sensation is rated as 0, 1, 2 or 3 with: 0 as no change; 1 as slight coolness, cold, or tingling; 2 as clear-cut signal of coolness, cold, or tingling; and 3 as robust cooling or cold. The intervals for recording sensations are 5 to 10 minutes, until two successive zeroes are obtained. The results (shown in FIGS. 1 and 2) are averaged values of 4 to 6 separate trials in the same individual. The data are plotted using SigmaPlot® (Systat Software, Point Richmond Calif.). Confirmatory trials of cooling action of some of the long-acting NADE compounds were obtained in 2 to 4 individuals.

The onset of drug action is taken as the time to reach 2 units of coolness intensity, and offset of drug action is the time when coolness intensity drops below 2, after previously surpassing 2 units. The duration of cooling action is defined as the offset time minus the onset time. An inactive compound is defined as one that does not exceed 2 units of cooling for 5 minutes at any time after application.

Additional Bioassay Procedures

To obtain additional information on bioactivity, end-points such as cooling the ocular surface and cough suppression were also measured. The ocular and pharyngeal surfaces are mucous membranes and the philtrum skin is keratinized.

Anti-Cough Activity. A number of cough challenge methods have been devised for evoking the cough reflex (Morice et al. Briti. J. Clin. Pharmacol. 52: 365-375, 2001). Usually, citric acid or capsaicin is delivered via the inhalation route to volunteers and the number of coughs counted. I have found that the sensations in the lower pharynx associated with the urge to cough can be replicated by placing (with a syringe or a plastic stick) 0.2 to 0.25 ml of a chili pepper sauce onto the posterior dorsal surface of the tongue. The chili pepper sauce used here is called Yank Sing® Chili Pepper Sauce (YS Gourmet Productions, Inc., PO Box 26189, San Francisco, Calif. 94126) and is a well-known condiment for use with dim sum (Chinese tea lunch). The sensations associated with the chili pepper sauce are located in the back of the mouth and are clearly recognized and associated with a desire to clear the throat.

The chili-pepper sauce evoked sensations can be readily suppressed with a drink of ice cold water or with an orally disintegrating tablet (ODD containing a cooling ingredient, but is not affected by an ODT containing only the excipient. To test for anti-cough activity the ODT with the test substance is first administered onto the dorsal surface of the tongue and 45 to 50 min afterwards the chili-pepper sauce test is administered. If there is no attenuation of the challenge stimuli, the score is 0, if there is partial inhibition, the score is +, and if there is complete attenuation of the cough signal, the score is ++. In the presence of an ODT that results in a ++ score, the irritative signals are completely absent, yet the salty taste used in the soy sauce of the condiment can still be easily tasted. The test substances in the ODT that produced a ++ score were then identified and compared to responses on the skin and the ocular surface.

Ocular Surface. To further document the activities of the test molecules, the results from an eye wipe test was included. Here the test substance is applied to the closed eyelids with a towelette in a 5%-ethanol-95%-distilled water (vol/vol) delivery vehicle at a concentration of 1 mg/ml and the duration of cooling on the ocular surface was recorded. Surprisingly, a good correlation was found between ocular cooling duration and anti-cough activity but less so with the duration of cooling based on the philtrum skin assay. It is likely that the mucous membranes that line the ocular surface and the pharynx have similar sensory mechanisms that are different from the philtrum skin which is keratinized.

Delivery to Target of N-Alkylcarbonyl-Alanyl Esters

In formulating compositions for the skin, the NADE compound of Formula 1 may be incorporated into a vehicle that by itself may be inert or may contain other active ingredients.

Suitable formulations, for example, include compositions such as liquids, pastes, lotions, liniments, creams and ointments, and cosmetic preparations. A wide variety of vehicles will be suitable, depending upon the particular product involved, such vehicles including solids, liquids, emulsions, foams and gels. Typical vehicles include oils and fats such as hydrocarbon oils, polyhdric alcohols, calcium or magnesium stearate, fatty acid esters, long chain alcohols and silicone oils; finely divided solids such as starch or talc; low-boiling hydrocarbons; gums and natural or synthetic resins.

The duration of action of the active preparation may be further enhanced and localized at its sites of action by the incorporation of mucoadhesive or bioadhesive agent. Typical adhesive molecules are polymers of sugars, alcohols, vinyl pyrrolidine, cellulose and the like. In practice, the long-acting NACE compound may also be applied onto the skin using a towelette that is of a construction sufficient or adapted to deliver the NACE compound to the skin. Thus, the desired NACE compound is suspended, dissolved, and/or dispersed so as to be in contact with the towelette. Suitable towelettes include a pad that may be of woven or nonwoven material usually in a unit dispenser. The wiping of the towelette or pad across skin results in delivery to the skin of dermatologically active ingredient(s), meaning that the skin is substantially medicated. Other drugs, cosmeceuticals, herbal medicines, traditional medicines, and active cosmetic ingredients suitable for topical human use may also be incorporated into the towelette.

It is contemplated that long-acting NACE compound may be incorporated into towelettes for treating the ageing skin; to treat the skin discomforts of acne, sunburn, fever, hyperthermia, fungal infections, yeast infections, xerotic eczema, rosacea, photodamaged skin; to reduce the discomforts of treatments for hyperpigmented skin, eczema, allergic or contact dermatitis, seborrheic dermatitis, mucositis, erythema, or psoriasis; and to be included with other dermatologic agents such as carboxylic acids, antibiotics, keratolytic agents or combinations thereof.

The ability of long-acting NACE compound to impart cooling and refreshment in a towelette without sting, burn or irritation (especially to the eyes), is an advance over current technology on cooling agents. Known towelettes frequently contain SD Alcohol (specially denatured alcohol; usually ethanol, isopropyl alcohol or methanol), which is present as a solvent and/or a cooling agent. Alcohol produces cooling when it abstracts heat from its environs during evaporation. The drawback of using short-chain carbon-alcohols in such formulations is that the alcohol dehydrates tissues and causes irritation. When such a towelette is used near the eyeball, the alcohol vapors irritate the eye surface. Similarly, menthol, camphor, eucalyptol, and other ingredients added to towelettes to produce fragrance and cooling also irritate the skin and eyes.

For delivery onto the skin, (R)-1,2-propanediol may be considered for use as an alternative solvent to racemic propanediol.

Study 1

Chemical Synthesis of N-Alkylcarbonyl-Alanyl Esters and Related Compounds

Many substituted amino acid esters may be obtained from commercial sources such Sigma-Aldrich Corp., St. Louis, Mo., USA. For example, L- or D-alanine methyl ester, are listed in the 2003-2004 Aldrich Catalog. The precursor, D-alanine ethyl ester is available from Indofine Chemicals, Co., Hillsborough, N.J. The precursors, D-alanine isopropyl, n-propyl ester, and n-butyl esters were custom synthesized (Phoenix Pharmaceuticals, Burlingame, Calif. and Diaharm Ltd., St. Petersburg, Russia). The acid chloride is reacted with the appropriate amino acid ester to form the NADE compound.

As an example of synthetic procedure, D-Ala methyl ester hydrochloride was obtained from Aldrich Chemical Co., 1.0 g was dissolved in 28 mL diethyether and 1 mL double-distilled water and cooled to 0° C. A pinch of the catalyst diaminopyrimidine was added. 1.62 mL of p-menthoyl chloride was then added dropwise, followed by 2 mL of triethylamine. Clumps of white precipitates appeared in the mixture, which was stirred overnight at room temperature. The precipitate was dissolved with ethyl acetate, washed with double-distilled water, and dried over sodium sulfate. The organic phase was then evaporated under reduced pressure to yield the final product (2 g), which crystallized at room temperature. The purity of the compound was checked by high-performance liquid chromatography. The expected molecular mass was then confirmed by mass spectroscopy and the absorption spectrum by nuclear magnetic resonance.

Test Results and Discussion

A number of compounds were tested (see U.S. 20080227857). Results (FIG. 1) illustrate the duration of cooling for five compounds (in order, left to right): WS-3, (−)-menthol, WS-5, D-Ala-OMe, and D-Ala-OEt. The known agents in commerce, e.g., (−)-menthol, WS-3, and WS-5 are active for ≤0.5 hr, and relatively short compared to the D-Ala-OMe and D-Ala-OEt analogs which were active >1.5 hr. D-Ala-OnPr and D-Ala-OnBu were also tested at 10 mg/ml in ointment, but in about 8 out 15 trials, the duration of action of these compounds exceeded 4 hr. The test subjects became distracted, took showers, or fell asleep, and continuous recording of cooling sensation was interrupted. Therefore, test results for these two analogs at 10 mg/ml are not graphed and a lower dose of 5 mg/ml in ointment (Table 3, philtrum skin column) was used for later trials. The compounds of Formula 1 were also tested in a liquid vehicle composed of 1% EtOH-99% (R)-1,2-propanediol.

The NADE compounds (FIG. 2), D-Ala-OMe, D-Ala-OEt, D-Ala-OnPr, and D-Ala-OnBu, have a refreshing cool, without skin or eye irritancy, and increased duration of action on the skin relative to menthol, WS-3 and WS-5 and other test substances. These NADE are examples of the preferred embodiments of this invention.

In the results of FIG. 1, the test compounds were singly applied to the skin above the upper lips as a ~1% wt/vol (10 mg/ml) ointment. Subsequently, for the results shown in FIG. 2 and Table 3, the test dose on the philtrum was a 0.5% wt/vol (5 mg/ml) ointment. As mentioned earlier, the reason for choosing a lower dose was to decrease the trial duration, to increase the number of trials per individual, and to have a reduced chance of substances accumulating in the skin. Subsequently, the philtrum evaluation of test compounds of Formula 1 were further simplified by testing in the 1% EtOH-99% (R)-1,2-propanediol vehicle.

TABLE 2

Summary of unique properties of NADE compounds of Formula 1 on skin in comparison with other compounds

| Chemical Class | Cooling on tongue | Cooling on skin of face | "perfect" cooling experience | Eye Irritancy | Activity >1 hr applied at 5 to 10 mg/ml |
|---|---|---|---|---|---|
| Long-acting NADE | yes | yes | yes | no | yes |
| other-NA carboxamides | yes | variable | no | yes | no |
| (−)-menthol | yes | yes | no | yes | no |
| SD alcohol | no | yes | yes | yes | no |

The principal findings from experiments are summarized in Table 2. The merits of the NADE compounds of Formula 1 relative to other compounds are the long duration of action in the absence of significant skin or ocular irritation.

The data of FIG. 2 and Table 3, tested at 5 mg/ml of ointment, confirm results of FIG. 1 that D-AlaOMe and D-AlaOEt have a long duration of action relative to other cooling compounds. Also, D-Ala-OnPr and D-Ala-OnBu were found to be active. The corresponding L-Ala analogs; L-Ala-OMe, L-Ala-OEt, L-Ala-OiPr, L-Ala-OnPr, and L-Ala-OnBu were much less active on the skin (Table 3 and 4).

The following p-menthane-alkyl carbonyl compounds were also tested at 5 mg/ml in Aquaphor® ointment on the philtrum skin: Gly-OMe, Gly-OEt, Gly-OnPr, Gly-OiPr, Gly-OnBu, β-Ala-OEt, and β-Ala-OiPr. None of these compounds matched the potency of the NADE compounds of Formula 1. The D-AlaO-n-pentyl, D-AlaO-n-hexyl, D-AlaO-n-heptyl analogs were also synthesized and found to be devoid of cooling activities on the skin.

Table 3. Bioassay results of substances applied to the philtrum skin in an ointment vehicle, to the eyelids with a towelette, and in response to a cough challenge. The test concentrations for the philtrum was 5 mg/ml in Aquaphor® ointment and the concentrations for the eye wipes was 1 mg/ml in 5%-95% v/v ethanol-distilled water. The duration of cooling is recorded as (minutes). In the chili-pepper sauce cough challenge test, the challenge was applied 45 to 50 min after the ODT which contained 2 mg of the test substance, and ++ indicates the ability of the test substance to suppress the cough sensations elicited by the pepper sauce. Compounds (no. 1, no. 2, no. 3 and no. 5) fulfill criteria of being a NADE compound for antipruritic/antinociceptive applications.

Formula (1)

R is methyl, ethyl, n-propyl, or n-butyl

| Compounds | R | Philtrum Skin (min) | Eyelids/Ocular Surface (min) | Chili-Pepper Sauce Test |
|---|---|---|---|---|
| D-Ala-OMe (no. 1) | Me | 77 | 120 | ++ |
| D-Ala-OEt (no. 2) | Et | 103 | 180 | ++ |
| D-Ala-OnPr (no. 3) | nPr | 108 | 65 | + |

-continued

Formula (1)

R is methyl, ethyl, n-propyl, or n-butyl

| Compounds | R | Philtrum Skin (min) | Eyelids/Ocular Surface (min) | Chili-Pepper Sauce Test |
|---|---|---|---|---|
| D-Ala-OiPr | iPr | 34 | 360 | ++ |
| D-Ala-OnBu (no. 4) | nBu | 80 | 40 | 0 |
| L-Ala-OMe | Me | 25 | 10 | 0 |
| L-Ala-OEt | Et | 34 | 0 | 0 |
| L-Ala-OiPr | iPr | 27 | 15 | 0 |
| L-Ala-OnPr | nPr | 22 | 10 | 0 |

Formula (1)

R is methyl, ethyl, n-propyl, or n-butyl

| Compounds | R | Philtrum Skin (min) | Eyelids/Ocular Surface (min) | Chili-Pepper Sauce Test |
|---|---|---|---|---|
| L-Ala-OnBu | nBu | 0 | 0 | |
| D-Nme-Ala-OEt | Et | 0 | 0 | 0 |

The D-Ala enantiomers: D-AlaOMe, D-AlaOEt, D-Ala-OiPr and D-Ala-OnPr, in addition to selective refreshing coolness with the absence of tissue irritation when applied to the skin, also cool the ocular surface, and suppress the cough sensations evoked by chili pepper sauce applied to the pharyngeal surface. The D-Ala-OnPr and D-Ala-OnBu analogs were much less active. Surprisingly, the L-Ala analogs. L-Ala-OMe, L-Ala-OEt, L-Ala-OiPr, L-Ala-OnPr, and L-Ala-OnBu were virtually devoid (<5%) of cooling activity on the ocular surface or on the pharyngeal surface, although some activity was seen on the philtrum assay. Thus, D-configuration of the α-carbon of Ala is an absolute requirement for potent cooling actions on the skin.

The correlation of activity among the in vivo bioassay endpoints depended on tissue characteristics. Thus, activity on the philtrum assay did not precisely predict activity on the ocular surface/pepper-sauce assays. For example, the D-Ala-OnPr and D-Ala-OnBu have a long duration of action on the philtrum skin, but this is not matched by increased potency on the ocular surface or on the pepper-sauce assay. On the other hand, the eye wipe test is highly correlated to activity on the pharyngeal surface. The differences in response may be due to differences in tissue architecture and sensory mechanisms. The ocular and pharyngeal surfaces are mucous membranes, but the philtrum skin is keratinized. For use in skin itch/pain, the D-Ala-OnPr and D-Ala-OnBu have a long duration of action on the philtrum skin and are the preferred compounds.

One unusual feature noted in the Studies of the NADE compounds of Formula 1 in human subjects is that the cooling action on the skin may dissipate, yet the antipruritic and antinociceptive effects lasts much longer. This "memory trace" action may be explained if it is clearly recognized that the antinociceptive action is indirect, acting via a gating mechanism. There is no direct drug action of the cooling agent on itch/air receptors in the skin. It is the cooling Aδ/C-fiber transmitted sensory signals that are triggering release an inhibitory process (perhaps via metabotropic glutamic acid receptors) that is gating the itch/pain signal. The gating mechanism in the central nervous system may desensitize, hyper-polarize, or otherwise modulate the sensitivity of central neurons for an extended period of time. That is, there is a lingering memory trace in the brain that attenuates the sensations of and/or the urge to scratch or complain of pain.

To describe this idea in lay terms, I use the analogy of going out into the spring sunshine for 15 min, being happy, and then coming back indoors. Although the skin is no longer warm after leaving the sun, the change in mood may last for several hours or longer. A pleasant cooling memory trace may thus reduce sensitivity to noxious stimuli (W. Wordsworth describes the power of a memory trace as: "They flash upon that inward eye, Which is the bliss of solitude; And then my heart with pleasure fills, And dances with the daffodils.").

Study 2

Formulation of Test Candidates in (R)-1,2-Propanediol for Testing on Skin.

Weil et al. 2005 [Molecular Pharmacology 68: 518-527, 2005] and Benedikt et al. 2007 [J. Neurochemistry 100: 211-224, 2007] have reported that certain alcohols can inhibit the response of the TRP-M8 receptor to menthol. The relative rank of potency for inhibition was butanol>isopropanol>ethanol>methanol. These studies show the solvent vehicle is important for the bioactivity of cooling agents.

I have explored the effects of solvents such as ethanol, n-propanol, isopropanol, 1,3-propanediol, 1,3-butanediol, (S)-propane-1,2-diol and (R)-propane-1,2-diol on the actions of cooling agents in the philtrum assay. Surprisingly, (R)-propane-1,2-diol, relative to these other solvents, is substantially devoid of inhibitory action. This phenomenon is dramatic and unexpected. Thus, (R)-propane-1,2-diol is an ideal solvent for cooling agents.

For the skin, a 1% ethanol-99% (R)-1,2-propanediol solvent containing the test substance at 5 mg/ml is an ideal formulation for testing cooling activity, using the coolness intensity index described previously. This solvent, unlike the Aquaphor® ointment, has less interacting variables and provide a simple method for quantifying the index of bioactivity. The results with various test substances are shown in FIG. 2 and in Table 4.

It can be seen in the results of Table 4 that the L-Ala-congeners were less active than the D-Ala-compounds. Three of the L-Ala-congeners did not reach a coolness intensity of "2 units" and were therefore considered inactive (=0). For no. 2 and no. 3, the maximum coolness intensity recorded was 2.2 units out of a possible 3. For a racemic mixture of Ala-OEt, one can estimate the contribution of the L-Ala-OEt to be 8/68 of the total activity or ~12%. The D-Ala-OEt enantiomer would contribute at least 88% of the total cooling activity. This stereoselectivity is greater for the D-Ala-OnPr (no. 3) and D-Ala-OnBu (no. 5) analogs.

Table 4. Comparison of D-Ala vs L-Ala N-alkylcarbonyl amino acid esters compounds on the philtrum assay. The test substance is dissolved in 1% EtOH-99% (R)-1,2-propanediol and ~0.03 ml is applied a surface area of ~11 cm². For a 5 mg/ml solution, the applied dose is ~0.15 mg/11 cm²=0.014 mg/cm². For an inflamed surface of about 100 cm² such as might occur on an elbow or knee flexure, the total total single dose is ~1.5 mg per application of a 0.5% or 5 mg/ml solution. The (R)-1,2-propanediol results cannot be directly compared to the Aquaphor® results because ~0.05 ml of Aquaphor® is applied versus ~0.03 ml for (R)-1,2-propanediol. The results for the D-Ala-analogs in this Table are plotted in FIG. 2. The rank order of potency is D-Ala-OnPr>D-Ala-OnBu>D-Ala-OEt>D-Ala-OiPr~D-Ala-OMe.

| Compounds | (min) | Compounds | (min) |
|---|---|---|---|
| L-Ala-OMe | 0 | D-Ala-OMe (no. 1) | 42 |
| L-Ala-OEt | 8 | D-Ala-OEt (no. 2) | 60 |
| L-Ala-OnPr | 10 | D-Ala-OnPr (no. 3) | 86 |
| L-Ala-OiPr | 0 | D-Ala-OiPr (no. 4) | 38 |
| L-Ala-OnBu | 0 | D-Ala-OnBu (no. 5) | 65 |

Study 3

Although D-Ala-OnPr and D-Ala-OiPr are D-Ala-enantiomers the duration of action of D-Ala-OnPr is significantly longer, being 2.26 times that of D-Ala-OiPr. To determine if the difference was due to pharmacokinetic parameters, the permeation rate of D-Ala-OnPr was examined in an in vitro model. Excised skin of hairless mice were placed on diffusion chambers coupled to a multi-channel peristaltic pump, a fraction collection, and a circulating water bath to maintain constant temperature at 37° C. D-Ala-OnPr was dissolved in various solvents/buffer and 0.3 ml was placed on the skin and collected in the other compartment every 4 hr for 24 hr and the samples analyzed for D-Ala-OiPr by HPLC. The solubility of D-Ala-OnPr in the 30% PEG-400 (pH 6 buffer) was 83 µg/ml and the average transfer rate across skin was found to be about 10 to 12 µg/cm$^2$ over a 12 to 16-hr period when D-Ala-OnPr was first dissolved in 1% EtOH-99% 1,2-propanediol and mixed with buffer. These results showed that the transdermal permeability rate of D-Ala-OnPr was very low and that pharmacokinetic characteristics are the most likely explanation of its long duration of action on receptors located in the skin.

Study 4

A 21-year old female suffered from atopic eczema since she was 4-years old. Over the years she learned how to control the symptoms of this condition, mainly itching skin on her knee and elbow flexures, by the use of emollient creams/ointments and low potency steroid medications. She was especially wary of higher potency steroids because she said these medications made her skin thin and easily broken, and susceptible to rashes and acneiform-like papules. She had a busy social schedule and was especially annoyed by itching around the nape of the neck and below her earlobes because she went to parties, movies, theater, concerts, and weddings, and it was not socially graceful to scratch vigorously in public. She agreed to try a towelette containing a NADE of Formula 1 to control her itch.

The towelette unit was a 0.4 g cotton rectangle (50 mm×60 mm) (CS-being, Daisan Cotton, Japan) to which was added two ml of a 1%-ethanol/99% (R)-1,2-propanediol solvent containing 5 mg/ml of D-Ala-OnPr (no. 3). The towelettes were individually sealed with a vaccuum apparatus and stored in the refrigerator (Foodsaver®, Jarden Corp.). For this subject, use of this medicated towelette was successful in controlling itch. She remarked that the towelette could be used discreetly, and the solvent did not leave a shiny residue on her skin. She said she now felt more confident in public situations.

Study 5

A 52-year old golfer went in June for a vacation to a famous resort in North Carolina and made the mistake of playing golf near the beaches late in the afternoon, dressed in shorts, without first applying an insect repellent. He received multiple bites below the knee from insects, most likely minute biting insects known commonly as "sandflies" or "no-see-ums." Later that night and into the next day, he developed an agonizing itch/pain on the skin of his lower legs and requested assistance. Upon examination of the skin of his lower legs, one could small red bumps (papules) and red welts. Along the socks-line, the skin was bloodied by excessive scratching with the finger-nails. The individual agreed to try an ointment containing 1% (wt/vol) of D-Ala-OEt (no. 2 in Table 1) in Aquaphor®. Suprisingly, the itch was significantly relieved within three minutes after application of the ointment. The individual still scratched his skin, but more gently, and with diminished intensity. He repeated applications of the ointment every hour together with a hydrocortisone cream which was later replaced by a more potent fluorinated steroid cream (Temovate®, 0.05% clobetasol propionate). He reported that "things were under control" and that he was ready to continue his vacation.

A 60-year male decided to move from California to Florida for retirement. He bought an old house near Jacksonville and decided to clean the large backyard. He accidentally disturbed a fire ant colony at the base of an old doghouse and received multiple bites on both of his forearms. These bites caused an immediate sharp pain on his forearm skin, following by burning sensations and itch. The individual applied an ointment containing 1% (wt/vol) D-Ala-OMe (no. 1 in Table 1) in Aquaphor® to the skin of his forearm, and the sensory discomfort was significantly relieved within five minutes after application. He further soaked his arms in a bucket of ice water and obtained relief from the pain. A day later, he felt all right and, although there were multiple small red blisters on his forearm skin from his encounter with fireants, he resumed work outdoors.

A 66-year male had two itchy mosquito bites on the skin below his olecranon (bony process of the elbow). This itch was completely suppressed for 10 hr after topical application of D-Ala-OnPr (no. 3 in Table 1), 0.5% in Aquaphor® ointment, using a cotton-tipped stick. No sensations of coolness were detected when this ointment was applied to the skin of either elbow, yet the itch was completely suppressed. This experimental observation is surprising. The skin at the elbow is quite thick relative to other keratinized surfaces of the body, e.g. the face, and may not have many receptive fields to detect the sensations of coolness. Yet, in the absence of coolness, a robust anti-pruritic effect was observed. From this observation, one may conclude that it is not necessary to feel coolness at the site of drug contact for the anti-pruritic effect to take place (this phenomenon was also observed on the scalp surface).

Study 6

A 64-year old male developed intense itch on the scalp at the base of the skull after use of hair dye (contact dermatitis). Application of D-Ala-OnPr (no. 3 in Table 1) or D-Ala-OnBu (no. 5 in Table 1), 0.5% in 1,2-RPD, using a cotton-ticked stick, suppressed the itch within 5 min of application and the effect lasted for at least 8 hr. Application of D-Ala-OnPr (no. 3) produced sensations of coolness on the scalp but this was barely noticeable with D-Ala-OnBu (no. 5). These results were surprising because the scalp has a thick epithelial layer and thermosensation is generally considered to be muted on the scalp. Thus, the NADE compound was diminishing the perception of nociceptive stimuli without the coolness sensations reaching consciousness. These results are potentially important for the management of scalp psoriasis, wherein itch and burning sensations in scalp lesions are sometimes a source of distress and discomfort.

Study 7

A 86-year old woman lived in a small well-heated apartment. During the winter time, she developed faint pink reticular changes on the skin of both lower legs, which then progressed to a deeper redness and cracking of the skin. The skin became irritated and itchy, and painful when scratched. She visited a dermatologist who specialized in cosmetic surgery. He took one glance at the skin below her knees, diagnosed it as "eczema craquelé", and dismissed her from the office with a prescription for fluocinolide 0.05% cream. She was reluctant to use the steroid cream because her elevated blood glucose indicated that she was a borderline diabetic; however, her itching skin kept her awake at night and created anxiety. She decided to try applications of a 0.5% D-Ala-OnPr (no. 3 in Table 1) ointment on the patches of her skin that itched. She said the itch was quickly relieved and that she was able to get a good night's sleep. She further consulted a more sympathetic general practitioner who had experience in geriatrics. He recommended that she use less soap during bathing. He showed her how to use moisturizing lotions, barrier creams, and a new anti-eczema cream containing 12% co-fatty acids. With these treatment procedures, and less scratching of the lesions, she felt much better, slept well, and the red, cracked skin on her legs disappeared after about five weeks and has not recurred one year after the initial episode.

The foregoing has described the principles, preferred embodiments, and modes of operation of the present invention. However, the invention should not be construed as limited to the particular embodiments discussed. Instead, the above-described embodiments should be regarded as illustrative rather than restrictive, and it should be appreciated that variations may be made in those embodiments by workers skilled in the art without departing from the scope of the present invention.

The invention claimed is:

1. A therapeutic method for selectively alleviating skin irritation, itch, and/or pain in a human comprising:
   providing a dermatological delivery vehicle including a therapeutically effective amount of (R)-2-[((1R,2S,5R)-2-isopropyl-5-methyl-cyclohexanecarbonyl)-amino]-propionic acid n-propyl ester; and
   contacting the delivery vehicle with the skin of a human, wherein the therapeutically effective amount is sufficient to alleviate skin irritation, itch and/or pain for at least three hours.

2. The method as in claim 1 wherein the (R)-2-R[((1R,2S,5R)-2-isopropyl-5-methyl-cyclohexanecarbonyl)-amino]-propionic acid n-propyl ester is in an amount of at least about 0.5% wt/vol of the delivery vehicle.

* * * * *